United States Patent
Stack et al.

[11] Patent Number: 5,126,367
[45] Date of Patent: Jun. 30, 1992

[54] PSYCHOTROPIC BENZODIOXAN DERIVATIVES

[75] Inventors: Gary P. Stack, Ambler; Magid A. Abou-Gharbia, Glen Mills; Wayne E. Childers, Jr., Yardley, all of Pa.

[73] Assignee: American Home Products Corporation, New York, N.Y.

[21] Appl. No.: 719,881

[22] Filed: Jun. 21, 1991

[51] Int. Cl.$^5$ ............... A61K 31/335; C07D 319/20
[52] U.S. Cl. .................. 514/452; 549/366; 549/407; 549/15
[58] Field of Search .............. 549/366; 514/452

[56] References Cited

U.S. PATENT DOCUMENTS

| | | | |
|---|---|---|---|
| 2,695,295 | 11/1954 | Swain | 549/366 |
| 2,725,386 | 11/1955 | Bovet et al. | 549/366 |
| 3,170,933 | 2/1965 | Schmidt | 549/366 |
| 3,324,143 | 6/1967 | Moed et al. | 549/366 |
| 4,684,739 | 8/1987 | Kikumoto et al. | 549/366 |
| 4,873,331 | 10/1989 | Childers et al. | 544/295 |
| 4,882,432 | 11/1989 | Abou-Gharbia et al. | 544/295 |
| 4,921,958 | 5/1990 | Abou-Gharbia et al. | 544/295 |
| 5,010,078 | 4/1991 | Abou-Gharbia et al. | 514/252 |
| 5,036,070 | 7/1991 | Abou-Gharbia | 514/252 |

FOREIGN PATENT DOCUMENTS

| | | |
|---|---|---|
| 170213 | 2/1986 | European Pat. Off. |
| 236930 | 9/1987 | European Pat. Off. |

OTHER PUBLICATIONS

Fozard et al., Br. J. Pharmacol. 90,273P (1987).

*Primary Examiner*—Nicky Chan
*Attorney, Agent, or Firm*—Richard K. Jackson

[57] ABSTRACT

A compound of the formula:

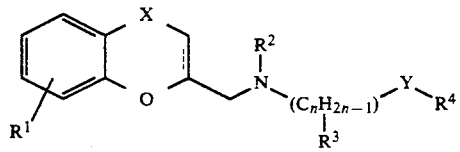

wherein the dotted line represents optional unsaturation; $R^1$ is hydrogen, alkyl, alkoxy, alkanoyloxy, hydroxy, halo, nitro, amino, alkylamino, dialkylamino and alkanoylamino; X is O, S or $CH_2$; n is an integer 2, 3 or 4; $R^2$ is hydrogen or lower alkyl; $R^3$ is hydrogen, lower alkyl, phenyl or benzyl; $R^4$ is one of the structures

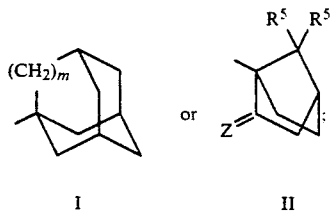

in which m is one of the integers 0, 1 or 2; $R^5$ is H or $CH_3$; Z is $H_2$ or O; Y is OCO, NHCO, NHCONH, CONH, and in addition, when $R^4$ is II, Y may be $NHSO_2CH_2$; or a pharmaceutically acceptable salt thereof are useful as antipsychotic/anxiolytic agents.

14 Claims, No Drawings

PSYCHOTROPIC BENZODIOXAN DERIVATIVES

BACKGROUND OF THE INVENTION

European Patent Application EP 170,213 discloses a series of glutarimide derivatives of benzodioxan methanamine as antianxiety and antihypertensive agents. Forzard et. al. Br. J. Pharmacol. 90, 273P (1987) disclose 8-[4-(1,4-benzodioxan-2-ylmethylamino)butyl]-8-azaspiro[4.5]decane-7,9-dione (MDL 72832) as a selective and stereospecific [(−)-MDL 72832 binds 32 times as much as the dextrorotary isomer at the 5-HT$_{1A}$ receptor site] ligand for 5-HT$_{1A}$ receptors.

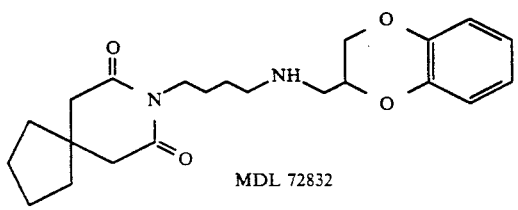

MDL 72832

European Patent EP 236,930 discloses a series of 2-substituted-alkyl-1,2-benzisothiazole-3-one 1,1-dioxide derivatives useful as anxiolytic and antihypertensive agents. Specifically claimed is 2-(4-(2,3-dihydro-1,4-benzodiox-2-yl)methylamino)butyl)-1,2-benzisothiazol-3(2H)-one 1,1-dioxide.

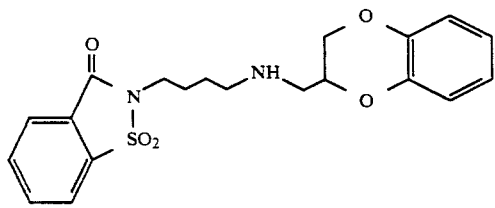

U.S. patent application Ser. No. 07/493,179, filed Mar. 14, 1990, now U.S. Pat. No. 5,010,078, describes adamantyl amide derivatives of aryl and heteroarylpiperazinylalkylamines as anxiolytic, antidepressant, and antihypertensive agents. U.S. Pat. Nos. 4,921,958, 4,873,331, and 4,882,432 describe other adamantyl esters, carbonates, ureas, urethans, and reverse amides for the same utilities.

DESCRIPTION OF THE INVENTION

In accordance with this invention, there is provided a group of novel antipsychotic/anxiolytic agents of the formula:

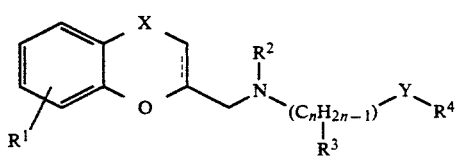

wherein the dotted line represents optional unsaturation;

$R^1$ is hydrogen, alkyl of 1 to 4 carbon atoms, alkoxy of 1 to 4 carbon atoms, alkanoyloxy of 2 to 4 carbon atoms, hydroxy, halo, nitro, amino, alkylamino of 1 to 4 carbon atoms, dialkylamino in which each alkyl group contains 1 to 4 carbon atoms and alkanoylamino of 2 to 4 carbon atoms;

X is O, S or CH$_2$;

n is an integer 2, 3 or 4;

$R^2$ is hydrogen or lower alkyl of 1 to 4 carbon atoms;

$R^3$ is hydrogen, lower alkyl of 1 to 4 carbon atoms, phenyl or benzyl;

$R^4$ is one of the structures

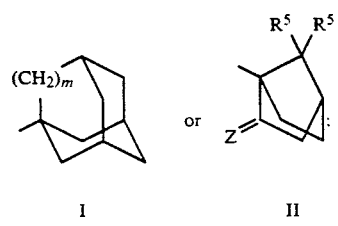

I  II in which m is one of the integers 0, 1 or 2;

$R^5$ is H or CH$_3$;

Z is H$_2$ or O;

Y is OCO, NHCO, NHCONH. CONH, and in addition, when $R^4$ is II, Y may be NHSO$_2$CH$_2$;

or a pharmaceutically acceptable salt thereof.

The group $R^3$ present in these compounds may appear on any one of the carbon atoms present in $C_nH_{2n-1}$. In a preferred position, it is on the carbon atom adjacent Y. In each position, when $R^3$ is other than hydrogen, a chiral center is formed by its presence. The resulting optically active isomers may be separated by standard procedures.

Of these compounds, the preferred members are those in which X is oxygen, $R^2$ and $R^3$ are hydrogen, the dotted line is omitted, and $R^1$, $R^4$, n and Y are defined as above. Most preferred are those members in which $R^1$, $R^2$ and $R^3$ are hydrogen, X is oxygen, the dotted line is omitted, n is 2 and $R^4$ and Y are defined as above.

The pharmaceutically acceptable salts are those derived from such organic and inorganic acids as: acetic, lactic, citric, tartaric, succinic, maleic, malonic, hydrochloric, hydrobromic, phosphoric, nitric, sulfuric, methanesulfonic, and similarly known acceptable acids.

The compounds of this invention are prepared by conventional methods. For example, the appropriately substituted benzodioxan methanamine is combined with a suitable acid or alkyl halide in the presence of an acid scavenger such as diisopropylethylamine (1), or with a suitable isocyanate, which itself can be generated in situ from the appropriate amine hydrochloride by treatment with trichloromethyl chloroformate in the presence of triethylamine (2).

(1) 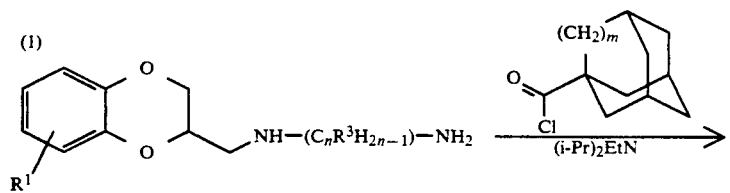

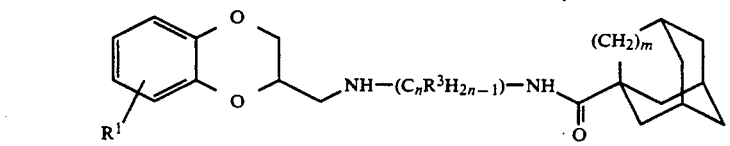

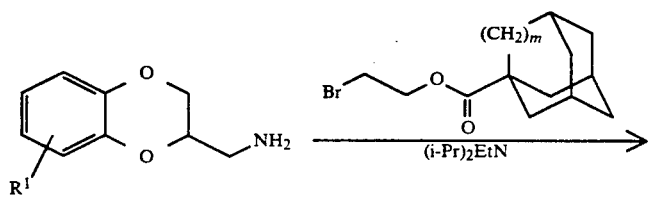

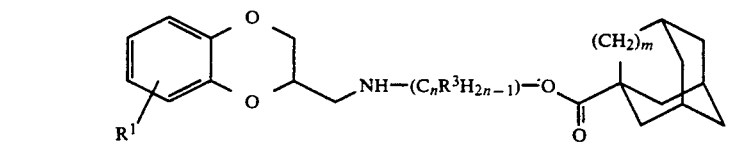

(2) 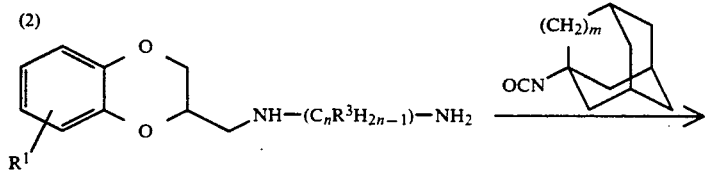

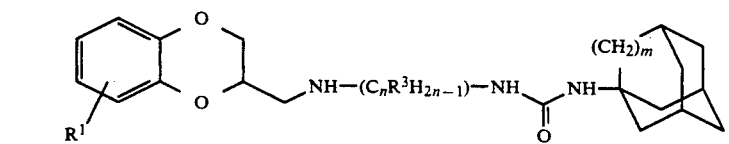

The bicyclic carboxylic acids and amines described by $R^4$ are known compounds or they can be readily synthesized by one schooled in the art. Adamantane and noradamantane-1-carboxylic acids and amines are commercially available; ketopinic acid can be prepared from camphorsulfonyl chloride by the method of Bartlett and Knox (Organic Synthesis, Vol 45, p. 55) and can be converted to apocamphane-1-carboxylic acid by the method described in J. Am. Chem. Soc., 61, 3184 (1939). The benzodioxan methanamines themselves are known compounds, or they can readily be derived from the appropriate salicylaldehyde by the procedure illustrated below:

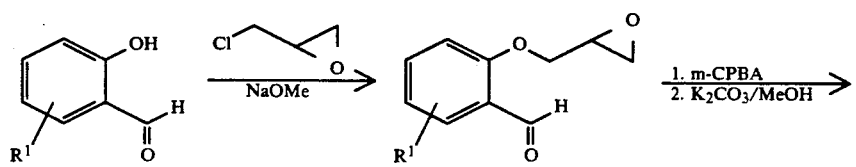

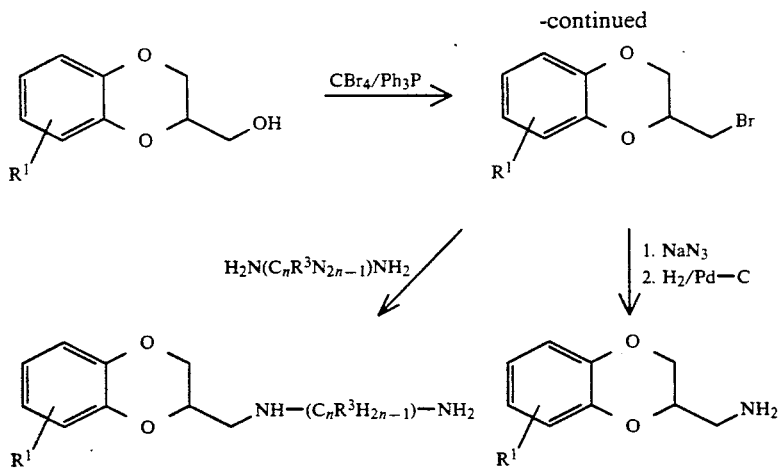

In these equations, m-CPBA is meta-chloroperbenzoic acid and $Ph_3P$ is triphenylphosphine.

The compounds of this invention possess high affinities for the dopamine D-2 receptor and the serotonin 5-HT$_{1A}$ receptor, and consequently, they are useful as antipsychotic, antidepressant and anxiolytic agents for the treatment of a variety of central nervous system disorders such as depression, paranoia, schizophrenia, anxiety, sleep disorders, sexual dysfunction, drug and alcohol addition (cocaine, heroine, etc.), and related problems.

High affinity for the dopamine $D_2$ receptor was established by the standard experimental test procedure of Fields, et al., Brain Res., 136, 578 (1977) and Yamamura et al., eds., Neurotransmitter Receptor Binding, Raven Press. New York (1978) wherein homogenized limbic brain tissue is incubated with $^3$H-spiroperidol and various concentrations of test compound, filtered and washed and shaken with Hydrofluor scintillation cocktail (National Diagnostics) and counted in a Packard 460 CD scintillation counter. The results of this testing with compounds representative of this invention are given below.

High affinity for the serotonin 5-HT$_{1A}$ receptor was established by testing the claimed compound's ability to displace [$^3$H] 8-OHDPAT (dipropylaminotetralin) from the 5-HT$_{1A}$ serotonin receptor following the procedure of Hall et al., J. Neurochem. 44, 1685 (1985). This procedure is employed to analogize this property of the claimed compounds with that of buspirone, which is a standard for anxiolytic activity, and, like the compounds of this invention, displays potent affinity for the 5-HT$_{1A}$ serotonin receptor subtype. The anxiolytic activity of buspirone is believed to be, at least partially, due to its 5-HT$_{1A}$ receptor affinity (Vander Maclen et al., Eur. J. Pharmacol. 1986, 129 (1-2) 133-130).

The results of the two standard experimental test procedures described in the preceding two paragraphs were as follows:

| Compound | D-2 Binding (% Inhibition at 1 μM) | 5-HT$_{1A}$ Binding (% Inhibition at 0.1 μM) |
|---|---|---|
| Example 1 | 83% | 100% |
| Example 2 | 91% | 100% |
| Example 3 | 27% | 98% (IC$_{50}$ = 5 nM) |
| Example 4 | 55% | 95% |
| Example 5 | 34% | 97% (EC$_{50}$ = 3 nM) |
| Example 6 | 34% | 88% |
| Example 7 | 81% | 98% |
| Example 8 | 49% | 90% (IC$_{50}$ = 9 nM) |

Certain of the compounds of this invention were also compared to buspirone in their ability to either produce or antagonize the serotonin syndrome according to the procedure of Smith and Peroutka, Pharmacol. Biochem. Behav. 24: 1513-1519, 1986, in which 250-350 g male Sprague-Dawley CD rats (Charles River) are given either test compound or vehicle and placed individually into plexiglass observation cages. Agonist activity of the compound is determined by scoring for the presence of the serotonin syndrome (forepaw treading, head weaving, tremor, hindlimb abduction, flattened body posture, and Straub tail) during the first 15 minutes after compound administration. Antagonist activity is then determined by a challenge with either of the 5-HT$_{1A}$ agonists 5-methoxy-N,N-dimethyltryptamine (5-MeODMT) or 8-hydroxydipropylaminotetralin. Buspirone produced the syndrome with an ED$_{50}$ of 7.3 mg/kg and antagonized 5-MeODMT-induced syndrome with an ED$_{50}$ of 4.6 mg/kg, and thus was characterized as a partial agonist. The compound of Example 5 by comparison induced the syndrome with an ED$_{50}$ of 3.8 mg/kg and antagonized 8-OH-DPAT induced syndrome with an ED$_{50}$ of 4.7 mg/kg. The compound of Example 6 was tested at a single dose of 20 mg/kg and also determined to be a partial agonist. The compound of Example 3 by contrast mimicked buspirone's ability to antagonize the serotonin syndrome at 1.0, 3.3, 10.0, and 33.0 mg/kg, but did not produce the syndrome on its own.

Hence, the compounds of this invention demonstrated high affinity for both the serotonin 5-HT$_{1A}$ and dopamine $D_2$ receptor subtypes, and are therefore useful in the treatment of multi-CNS disorders amenable to treatment with antipsychotic, antidepressant and anxiolytic agents. They may be administered orally or parenterally, neat or with a pharmaceutical carrier to a patient suffering from central nervous system disorders amenable to treatment with antipsychotic, anxiolytic, antidepressant agents which function via the dopamine D-2 and serotonin 5-HT$_{1A}$ receptors.

Applicable solid carriers can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The dosage to be used in the treatment of a specific psychosis must be subjectively determined by the attending physician. The variables involved include the specific psychosis or state of anxiety or depression and the size, age and response pattern of the patient.

The following examples illustrate the production of representative compounds of this invention.

EXAMPLE 1

N-[2-[[(2,3-Dihydro-1,4-benzodioxin-2-yl)methyl]amino]ethyl]tricyclo[3,3,1,1(3,7)]-decane-1-carboxamide Adamantane-1-carboxylic acid (1.7 g, 10 mmole) was dissolved in 100 ml of dichloromethane and 3 drops of DMF added. Oxalyl chloride (2.0 ml, 23 mmole) was added and the mixture was stirred at room temperature for 2 hours. An additional 1.0 ml of oxalyl chloride (11.5 mmole) was then added, and stirring continued for 30 minutes. The mixture was concentrated to dryness in vacuum. 2-{N-(2-aminoethyl)]aminomethyl-2,3-dihydrobenzodioxin (2.1 g, 10 mmole) was dissolved in 100 ml of methylene chloride and 1.3 g (10 mmole) of diisopropylethylamine was added. To this mixture was added the acid chloride prepared above as a solution in 50 ml of dichloromethane. The addition was performed at 0° C. over 5 minutes. The mixture was then stirred overnight at room temperature. The reaction was next washed with saturated aqueous sodium bicarbonate, with saturated sodium chloride, dried over sodium sulfate, filtered and evaporated in vacuum. Column chromatography on 100 g of silica gel with chloroform as eluant, followed by crystallization from 100 ml of isopropanol with addition of 5 ml of 4N isopropanolic HCl and 400 ml of diethyl ether gave 1.3 g of the title compound as a monohydrochloride ¼ hydrate, m.p. 147°–149° C.

Elemental Analysis for: $C_{22}H_{30}N_2O_3 \cdot HCl \cdot \frac{1}{4}H_2O$
Calc'd: C, 64.22; H, 7.72; N, 6.81
Found: C, 64.15; H, 7.68; N, 6.63

EXAMPLE 2

Tricyclo[3,3,1,1(3,7)]decane-1-carboxylic acid 2-[[(2,3-dihydro-1,4-benzodioxin-2-yl)methyl]amino]ethyl ester To a solution of 2-aminomethyl-1,4-benzodioxan (0.99 g, 60 mmole) in DMF (48 ml) was added adamantane-1-(2-bromoethyl)carboxylate (1.16 g, 40.4 mmole) and diisopropylethylamine (9.0 ml, 6.7 g, 52 mmole). The solution was stirred for 2 days at 35°–40° C., for one day at 57° C. and one day at 97° C. The DMF was then removed under reduced pressure. The residue was dissolved in methylene choride and washed with water. The aqueous wash was back-extracted with methylene chloride, and the combined organic phases were washed with saturated NaCl solution and dried over MgSO₄. Filtration and concentration in vacuum gave 2.25 g of crude product, which was purified by HPLC to yield 0.31 g of the desired free base. Treatment of an ethanol solution of the compound with excess ethereal HCl gave 0.23 g of the title compound as a monohydrochloride, m.p. 146°–147° C.

Elemental Analysis for: $C_{22}H_{29}NO_4 \cdot HCl$
Calc'd: C, 64.78; H, 7.41; N, 3.43
Found: C, 64.43; H, 7.58; N, 3.31

EXAMPLE 3

N-[2-[(2,3-Dihydro-1,4-benzodioxin-2-yl)methylamino]ethyl]-N'-tricyclo[3,3,1,1(3,7)]dec-1-ylurea A stirred solution of 1-adamantamine hydrochloride (0.72 g, 3.8 mmole) and triethylamine (1.6 g, 15 mmole) in 25 ml of dry dichloromethane was refluxed under a dry nitrogen atmosphere at 60° C. for 30 minutes. The resulting mixture was cooled to room temperature, trichloromethyl chloroformate (0.47 ml, 2 mmole) was added via syringe, and reflux was then continued for 3 hours. A solution of 2-[N-(2-aminoethyl)]aminomethyl-2,3-dihydrobenzodioxan (0.80 g, 3.8 mmole) in 10 ml of dry dichloromethane was then added and the reaction mixture was refluxed at 60° for two days. The mixture was then diluted to 150 ml with dichloromethane and washed with 100 ml of 5% aqueous sodium bicarbonate. The organic layer was dried over anhydrous sodium sulfate and concentrated in vacuum. The desire product (TLC on silica gel using 20% methanol in ethyl acetate, Rf=0.43) was isolated by column chromatography on silica gel using 20% methanol in ethyl acetate and converted to the dihydrochloride salt with isopropanolic HCl (0.76 g, 44% yield), m.p. 169°-170° C.

Elemental Analysis for: $C_{22}H_{31}N_3O_3.2HCl$
Calc'd: C, 57.64; H, 7.25; N, 9.16
Found: C, 57.41; H, 7.52; N, 9.52

EXAMPLE 4

N-[2-[(2,3-Dihydro-1,4-benzodioxin-2-yl)methyl]aminoethyl-N'-hexahydro-2,5-methanopentalen-3a(1H)-yl]urea A stirred solution of 3-noradamantamine hydrochloride (1.0 g, 5.7 mmole) and triethylamine (2.4 g, 23 mmole) in 25 ml of dry dichloromethane was refluxed under a dry nitrogen atmosphere at 60° C. for 30 minutes. The resulting mixture was cooled to room temperature, trichloromethyl chloroformate (0.70 ml, 2.8 mmole) was added via syringe, and reflux was then continued for 3 hours. A solution of 2-[N-(2-aminoethyl)]aminomethyl-2,3-dihydrobenzodioxin (1.2 g, 5.7 mmole) in 10 ml of dry dichloromethane was then added and the reaction mixture was stirred at room temperature for two days. The mixture was then diluted to 200 ml with dichloromethane and washed with 100 ml of 5% aqueous sodium bicarbonate. The organic layer was dried over anhydrous sodium sulfate and concentrated in vacuum. The desired product (TLC on silica gel using 30% methanol in ethyl acetate, Rf=0.32) was isolated by column chromatography on silica gel using 30% methanol in ethyl acetate and coverted to the dihydrochloride salt with isopropanolic HCl (0.83 g, 33% yield), m.p. 135°-137° C.

Elemental Analysis for: $C_{21}H_{29}N_3O_3.2HCl$
Calc'd: C, 56.70; H, 6.97; N, 9.45
Found: C, 56.94; H, 7.10; N, 9.61

EXAMPLE 5

(+)-N-[2-[[(2,3-Dihydro-1,4-benzodioxin-2-yl)methyl]amino]ethyl]-7,7-dimethyl-2-oxobicyclo[2,2,1]heptane-1-carboxamide (+)-Ketopinic acid (900 mg, 5.0 mmole), prepared from (+)-10-camphorsulfonyl chloride by the procedure of Bartlett and Knox, Org. Syn., 45, p. 55, was converted to the acid chloride by treatment of a solution of the compound in 50 ml of methylene chloride with 1.0 ml (11.5 mmole) of oxalyl chloride. After stirring for 2 hours at room temperature, the mixture was concentrated in vacuum. It was then redissolved in 50 ml of methylenechloride and added at 0° C. to a solution of 1.04 g (10 mmole) of 2-[N-(2-aminoethyl)]aminomethyl-2,3-dihydrobenzodioxin and 1.3 g (10 mmole) of diisopropylethylamine in 50 ml of dichloromethane. After stirring overnight at room temperature, the mixture was washed with saturated sodium bicarbonate solution, with saturated sodium chloride, dried over sodium sulfate, filtered and concentrated in vacuum. The residue was column chromatographed on 75 g of silica gel with chloroform as eluant and the title compound crystallized from isopropanol with the addition of 4 N HCl/isopropyl alcohol and 3 volumes of diethyl ether. This procedure gave 835 mg of title compound as the monohydrochloride, m.p. 172°-173° C., with an $[\alpha]_D^{25}=+32.7$ (MeOH).

Elemental Analysis for: $C_{21}H_{28}N_2O_4.HCl$
Calc'd: C, 61.68; H, 7.15; N, 6.85
Found: C, 61.84; H, 7.11; N, 6.82

EXAMPLE 6

((-)-N-[2-[[(2,3-Dihydro-1,4-benzodioxin-2-yl)methyl]amino]ethyl]-7,7-dimethyl-2-oxobicyclo[2,2,1]heptane-1-carboxamide To 2.0 g (10 mmole) (-)-ketopinic acid in 100 ml of dichloromethane was added 2.0 ml (23 mmole) oxalyl choride and 2 drops of DMF. The mixture was stirred for two hours at room temperature and then concentrated to dryness in vacuum. It was redissolved in 50 ml of methylenechloride and added to a cold solution of 2.1 g (10 mmole) 2-[N-(2-aminoethyl)]aminomethyl-2,3-dihydrobenzodioxin and 1.3 g (10 mmole) diisopropylethylamine in 100 ml of dichloromethane. The mixture was stirred at room temperature overnight. It was then washed with saturated aqueous sodium bicarbonate, with saturated sodium chloride, dried over sodium sulfate, filtered and evaporated in vacuum. The residue was column chromatographed on 100 g of silica gel with chloroform as eluant, and the product crystallized from 75 ml of isopropanol with the addition of 4 ml 4 N HCl/isopropyl alcohol and 225 ml of diethyl ether to produce 1.25 g of the title compound as the hydrochloride, quarter hydrate, m.p. 164°-166° C., $[\alpha]_D^{25}=-31.3$ (MeOH).

Elemental Analysis for: $C_{21}H_{28}N_2O_4.HCl.\frac{1}{4}H_2O$
Calc'd: C, 61.00; H, 7.19; N, 6.78
Found: C, 60.99; H, 7.09; N, 6.60

EXAMPLE 7

N-[2-[[(2,3-Dihydro-1,4-benzodioxin-2-yl)methyl]amino]ethyl]hexahydro-2,5-methanopentalene-3a(1H)-carboxamide To 500 mg (3.0 mmole) of noradamantane carboxylic acid in 50 ml of dichloromethane was added 1.0 ml (11.5 mmole) of oxalyl chloride and two drops of DMF. The mixture was stirred at room temperature for two hours and then concentrated in vacuum. It was redissolved in 20 ml of dichloromethane and added to an ice cold solution of 620 mg (3.0 mmole) 2-[N-(2-aminoethyl)]aminomethyl-2,3-dihydrobenzodioxin and 650 mg (5.0 mmole) diisopropylethylamine in 100 ml of dichloromethane. The mixture was allowed to stir overnight at room temperature. It was then washed with saturated sodium bicarbonate solution, with saturated brine, dried over sodium sulfate, filtered and concentrated in vacuum. The residue was column chromatographed on 50 g of silica gel with chloroform as eluant, and the product crystallized from isopropanol with the addition of 4 N HCl/IPA and 3 volumes of ether. This yielded 300 mg of title compound as the monohydrochloride, ¼ hydrate, m.p. 143°-144° C.

Elemental Analysis for: $C_{21}H_{28}N_2O_3.HCl.\frac{1}{4}H_2O$
Calc'd: C, 63.46; H, 7.48; N, 7.05
Found: C, 63.44; H, 7.47; N, 7.15

EXAMPLE 8

(1R)-(-)-N-[2-[[(2,3-Dihydro-1,4-benzodioxin-2-yl)methyl]amino]ethyl]-7,7-dimethyl-2-oxobicyclo[2,2,1]heptane-1-methanesulfonamide To a solution of 2.1 g (10 mmole) of 2-{N-(2-aminoethyl)]aminomethyl-2,3-dihydrobenzodioxin and 1.3 g (10 mmole) of diisopropylethylamine in 100 ml of dichloromethane stored in an ice bath was added 1.8 g (7.2 mmole) (-)-10-camphorsulfonyl chloride. The mixture was allowed to stir overnight at room temperature. The reaction was next washed with saturated aqueous sodium bicarbonate, with saturated sodium chloride, dried over sodium sulfate, filtered and evaporated in vacuum. Column chromatography on 100 g of silica gel with chloroform as eluant, followed by crystallization from isopropanol gave 1.3 g of the title compound, m.p. 149°–152° C.

Elemental Analysis for: $C_{21}H_{30}N_2O_5S$
Calc'd: C, 59.69; H, 7.15; N, 6.63
Found: C, 59.03; H, 6.89; N, 6.05

EXAMPLE 9

(1S)-(+)-N-[2-[[(2,3-Dihydro-1,4-benzodioxin-2-yl)methyl]amino]ethyl]-7,7-dimethyl-2-oxobicyclo[2,2,1]heptane-1-methanesulfonamide To a solution of 2.1 g (10 mmole) of 2-{N-(2-aminoethyl)]aminomethyl-2,3-dihydrobenzodioxin and 1.3 g (10 mmole) of diisopropylethylamine in 100 ml of dichloromethane stored in an ice bath was added 2.5 g (10 mmole) (+)-10-camphorsulfonyl chloride. The mixture was allowed to stir overnight at room temperature. The reaction was next washed with saturated aqueous sodium bicarbonate, with saturated sodium chloride, dried over sodium sulfate, filtered and evaporated in vacuum. Column chromatography on 75 g of silica gel with chloroform as eluant, followed by crystallization from 100 ml of isopropanol with the addition of 5 ml of 4 N HCl/isopropyl alcohol and 300 ml of diethyl ether gave 1.2 g of the title compound as a monohydrochloride, m.p. 143°–146° C.

Elemental Analysis for: $C_{21}H_{30}N_2O_5S \cdot HCl$
Calc'd: C, 54.95; H, 6.81; N, 6.10
Found: C, 54.60; H, 6.40; N, 6.15

What is claimed is:

1. A compound of the formula:

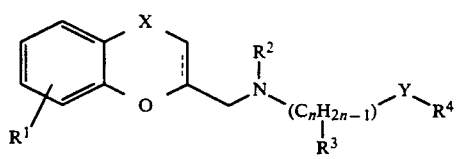

wherein
the dotted line represents optional unsaturation;
$R^1$ is hydrogen, alkyl of 1 to 4 carbon atoms, alkoxy of 1 to 4 carbon atoms, alkanoyloxy of 2 to 4 carbon atoms, hydroxy, halo, nitro, amino, alkylamino of 1 to 4 carbon atoms, dialkylamino in which each alkyl group contains 1 to 4 carbon atoms and alkanoylamino of 2 to 4 carbon atoms;
X is O
n is an integer 2,3 or 4;
$R^2$ is hydrogen or lower alkyl of 1 to 4 carbon atoms;
$R^3$ is hydrogen, lower alkyl of 1 to 4 carbon atoms, phenyl or benzyl;
$R^4$ is one of the structures

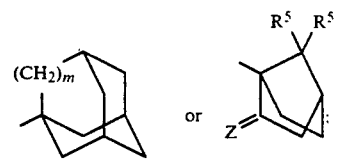

in which
m is one of the integers 0, 1 or 2;
$R^5$ is H or $CH_3$;
Z is $H_2$ or O;
Y is OCO, NHCO, NHCONH, CONH, and in addition, when $R^4$ is II, Y may be $NHSO_2CH_2$;
or a pharmaceutically acceptable salt thereof.

2. A compound of claim 1 in which the dotted line is omitted, $R^2$ and $R^3$ are hydrogen.

3. A compound of claim 1 in which the dotted line is omitted; $R^1$, $R^2$ and $R^3$ are hydrogen; and n is 2.

4. The compound of claim 1 which is N-[2-[[(2,3-dihydro-1,4-benzodioxin-2-yl)methyl]amino]ethyl]-tricyclo[3.3.1.1(3,7)]-decane-1-carboxamide, or a pharmaceutically acceptable salt thereof.

5. The compound of claim 1 which is tricyclo[3.3.1.1(3,7)]decane-1-carboxylic acid 2-[[(2,3-dihydro-1,4-benzodioxin-2-yl)methyl]amino]ethyl ester, or a pharmaceutically acceptable salt thereof.

6. The compound of claim 1 which is N-[2-[(2,3-dihydro-1,4-benzodioxin-2-yl)methylamino]ethyl]-N'-tricyclo[3.3.1.1(3,7)]dec-1-ylurea, or a pharmaceutically acceptable salt thereof.

7. The compound of claim 1 which is N-[2-[(2,3-dihydro-1,4-benzodioxin-2-yl)methyl]aminoethyl-N'-hexahydro-2,5-methanopentalen-3a(1H)-yl]urea, or a pharmaceutically acceptable salt thereof.

8. The compound of claim 1 which is (+)-N-[2-]](2,3-dihydro-1,4-benzodioxin-2-yl)methyl]amino]ethyl]-7,7-dimethyl-2-oxobicyclo[2.2.1]heptane-1-carboxamide, or a pharmaceutically acceptable salt thereof.

9. The compound of claim 1 which is ((−)-N-[2-[[(2,3-dihydro-1,4-benzodioxin-2-yl)methyl]amino]ethyl]-7,7-dimethyl-2-oxobicyclo[2.2.1]heptane-1-carboxamide, or a pharmaceutically acceptable salt thereof.

10. The compound of claim 1 which is N-[2-[[(2,3-dihydro-1,4-benzodioxin-2-yl)methyl]amino]ethyl]hexahydro-2,5-methanopentalene-3a(1H)-carboxamide, or a pharmaceutically acceptable salt thereof.

11. The compound of claim 1 which is (1R)-(−)-N-[2-[[(2,3-dihydro-1,4-benzodioxin-2-yl)methyl]amino]ethyl]-7,7-dimethyl-2-oxobicyclo[2.2.1]heptane-1-methanesulfonamide, or a pharmaceutically acceptable salt thereof.

12. The compound of claim 1 which is (1S)-(+)-N-[2-[[(2,3-dihydro-1,4-benzodioxin-2-yl)methyl]amino]ethyl]-7,7-dimethyl-2-oxbicyclo[2.2.1]heptane-1-methanesulfonamide, or a pharmaceutically acceptable salt thereof.

13. A method for the symptomatic treatment of central-nervous system disorders regulated by the dopamine $D_2$ receptor or the serotonin $5\text{-HT}_{1A}$ receptor, which comprises administering orally or parenterally to a mammal in need thereof, an antipsychotic, anxiolytic, or antidepressant effective amount of a compound of the formula:

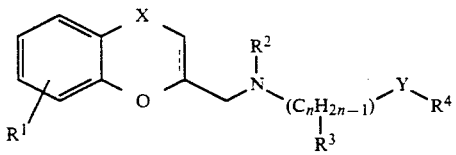

wherein
the dotted line represents optional unsaturation;
$R^1$ is hydrogen, alkyl of 1 to 4 carbon atoms, alkoxy of 1 to 4 carbon atoms, alkanoyloxy of 2 to 4 carbon atoms, hydroxy, halo, nitro, amino, alkylamino of 1 to 4 carbon atoms, dialkylamino in which each alkyl group contains 1 to 4 carbon atoms and alkanoylamino of 2 to 4 carbon atoms;
X is O;
n is an integer 2, 3 or 4;
$R^2$ is hydrogen or lower alkyl of 1 to 4 carbon atoms;
$R^3$ is hydrogen, lower alkyl of 1 to 4 carbon atoms, phenyl or benzyl;
$R^4$ is one of the structures

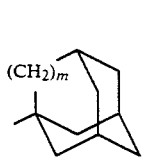    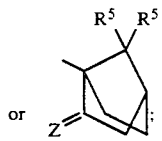

I    or    II in which
m is one of the integers 0, 1 or 2;
$R^5$ is H or $CH_3$;
Z is $H_2$ or O;
Y is OCO, NHCO, NHCONH, CONH, and in addition, when $R^4$ is II, Y may be $NHSO_2CH_2$;
or a pharmaceutically acceptable salt thereof.

14. A pharmaceutical composition comprising an antipsychotic, anxiolytic or antidepressant amount of a compound of the formula:

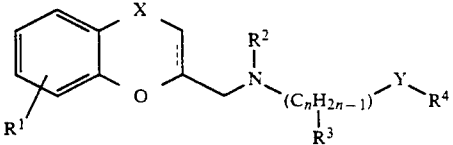

wherein
the dotted line represents optional unsaturation;
$R^1$ is hydrogen, alkyl of 1 to 4 carbon atoms, alkoxy of 1 to 4 carbon atoms, alkanoyloxy of 2 to 4 carbon atoms, hydroxy, halo, nitro, amino, alkylamino of 1 to 4 carbon atoms, dialkylamino in which each alkyl group contains 1 to 4 carbon atoms and alkanoylamino of 2 to 4 carbon atoms;
X is O;
n is an integer 2, 3 or 4;
$R^2$ is hydrogen or lower alkyl of 1 to 4 carbon atoms;
$R^3$ is hydrogen, lower alkyl of 1 to 4 carbon atoms, phenyl or benzyl;
$R^4$ is one of the structures

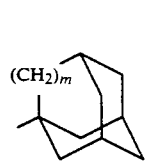    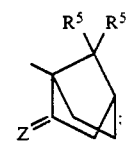

I    or    II in which
m is one of the integers 0, 1 or 2;
$R^5$ is H or $CH_3$;
Z is $H_2$ or O;
Y is OCO, NHCO, NHCONH, CONH, and in addition, when $R^4$ is II, Y may be $NHSO_2CH_2$;
and a pharmaceutically acceptable carrier.

* * * * *